United States Patent [19]

Iezzi et al.

[11] Patent Number: 5,414,182
[45] Date of Patent: May 9, 1995

[54] PROCESS FOR ACTIVATING CATALYST PERCURSORS FOR THE DEHYDROGENATION OF $C_2$-$C_5$ PARAFFINS, AND A CATALYTIC COMPOSITION ACTIVATED BY THE PROCESS

[75] Inventors: Rodolfo Iezzi; Andrea Bartolini; Franco Buonomo, all of San Donato Milanese, Italy

[73] Assignees: Snamprogetti S.p.A.; Eniricerche S.p.A., both of Milan, Italy

[21] Appl. No.: 194,390

[22] Filed: Feb. 10, 1994

Related U.S. Application Data

[62] Division of Ser. No. 27,944, Mar. 8, 1993, Pat. No. 5,308,822.

[30] Foreign Application Priority Data

Mar. 11, 1992 [IT] Italy .................... MI92U0558

[51] Int. Cl.$^6$ ............................................. C07C 5/333
[52] U.S. Cl. ..................................... 585/661; 585/654; 585/671
[58] Field of Search ......................... 585/654, 661, 671

[56] References Cited

U.S. PATENT DOCUMENTS 4,581,343 4/1986 Blanchard et al. ............... 502/241
4,588,705 5/1986 Vanderspurt et al. ............. 502/177

Primary Examiner—Helen M. S. Sneed
Assistant Examiner—E. D. Irzinski
Attorney, Agent, or Firm—Oblon, Spivak, McClelland, Maier, & Neustadt

[57] ABSTRACT

The process for activating a catalytic composition for paraffin dehydrogenation containing gallium, alumina, possibly silica and/or one or more alkaline or alkaline-earth metals, comprises thermal activation in air followed by post-activation effected by the following stages:
  oxidation with air and/or oxygen or a mixture containing oxygen and inert gas;
  purging with inert gas;
  reduction with hydrogen or a mixture of hydrogen and an inert or reducing gas.

The catalytic composition activated by said process contains gallium, alumina, silica and possibly one or more alkaline or alkaline-earth metals, the alumina being in $\delta$ or $\theta$ phase or in $\delta+\theta$ or $\delta+\theta+\alpha$ phase mixture.

16 Claims, 4 Drawing Sheets

PROCESS FOR ACTIVATING CATALYST PRECURSORS FOR THE DEHYDROGENATION OF $C_2$-$C_5$ PARAFFINS, AND A CATALYTIC COMPOSITION ACTIVATED BY THE PROCESS

This is a division of application Ser. No. 08/027,944, filed on Mar. 8, 1993, and now U.S. Pat. No. 5,308,822.

This invention relates mainly to a process for activating catalyst precursors for dehydrogenating $C_2$-$C_5$ paraffins (ie with between 2 and 5 carbon atoms) to the corresponding olefins, and to a catalytic composition activated by said process.

Olefins are important intermediaries in the production of widely used chemicals such as polypropylene, antiknock additives (MTBE), high-octane gasolines, alkylated derivatives and numerous other products.

Notwithstanding the growth in the demand for these derivatives, the expansion of industrial processes for their preparation is often limited by the poor availability of olefins, for example isobutene in MTBE production.

This has lead to the identification of other olefin sources in addition to the conventional sources (FCC, crackers). Of these, that which is assuming an ever increasing role is the dehydrogenation of light paraffins. Although this is simple in stoichiometric terms, it suffers from both thermodynamic and kinetic problems.

The reaction is endothermic and is governed by the thermodynamic equilibrium; For example it requires a temperature exceeding 500° C. for dehydrogenating $C_2$-$C_4$ paraffins with an economically acceptable conversion per pass. In addition, heat has to be supplied to the system to satisfy the endothermic nature of the reaction.

In spite of the high operating temperature, the dehydrogenation rate is low and it is therefore necessary to operate in the presence of a suitable catalyst. This must be thermally stable and able to provide high selectivity towards the desired olefin, while minimizing the isomerization, cracking and coking side reactions.

The inevitable formation of coke on the catalyst results in progressive reduction of catalytic activity, so that periodic regeneration is required.

The formulation must consequently present high stability under the conditions to which it is subjected during the reaction and regeneration.

Considerable effort has been expended in identifying catalytic compositions which satisfy the requirements of the particular type of process. In this respect, the patent literature describes numerous catalytic compositions either based on noble metals or combined with other chemical species (U.S. Pat. Nos. 3531543, 4786625, 4886928, EP 351067), or based on metal oxides in the presence of promoters, and consisting mostly of supported $Cr_2O_3$ (U.S. Pat. Nos. 2945823, 2956030, 2991255, GB 2162082). However both formulations have drawbacks. Those based on noble metals require special treatment during regeneration (U.S. Pat. No. 4438288) to preserve the dehydrogenating activity of the metal species. Those based on chromium oxide suffer from environmental problems and a reduction of activity with time if not suitably stabilized.

In recent years numerous patents have been published using catalytic compositions containing gallium (or its compounds) for dehydrogenating paraffins (U.S. Pat. No. 4056576) or for aromatizing paraffins (AU 509825, AU 565365, U.S. Pat. No. 4704494) from which unsaturated compounds are obtained with low conversion and low olefin selectivity.

We have now surprisingly discovered a new process for activating gallium-containing catalysts which when thus activated and used in $C_2$-$C_5$ paraffin dehydrogenation processes enable a substantially higher conversion and in particular selectivity to be obtained. The main aspect of the present invention is a process for activating catalyst precursors containing gallium, alumina, possibly silica and/or one or more alkaline or alkaline-earth metals, comprising thermal activation in air at a temperature of between 450° and 1000° C., followed by post-activation comprising the following stages:

oxidation with air and/or oxygen or a mixture containing oxygen at least in a 5 vol % concentration in an inert gas, for a time of between 1 and 180 minutes and preferably between 30 and 90 minutes, at a temperature of between 500° and 1000° C. and preferably between 550° and 700° C.;

purging with an inert gas for a time of between 1 and 10 minutes and preferably between 3 and 5 minutes;

reduction with hydrogen or a mixture containing hydrogen in at least a 10 vol % concentration in an inert or reducing gas, for a time of between 1 and 120 minutes and preferably between 30 and 90 minutes, at a temperature of between 450° and 800° C. and preferably between 500° and 700° C.

The inert gas used can be nitrogen, argon or helium, and for the purging can also be $CO_2$.

Figure 1:
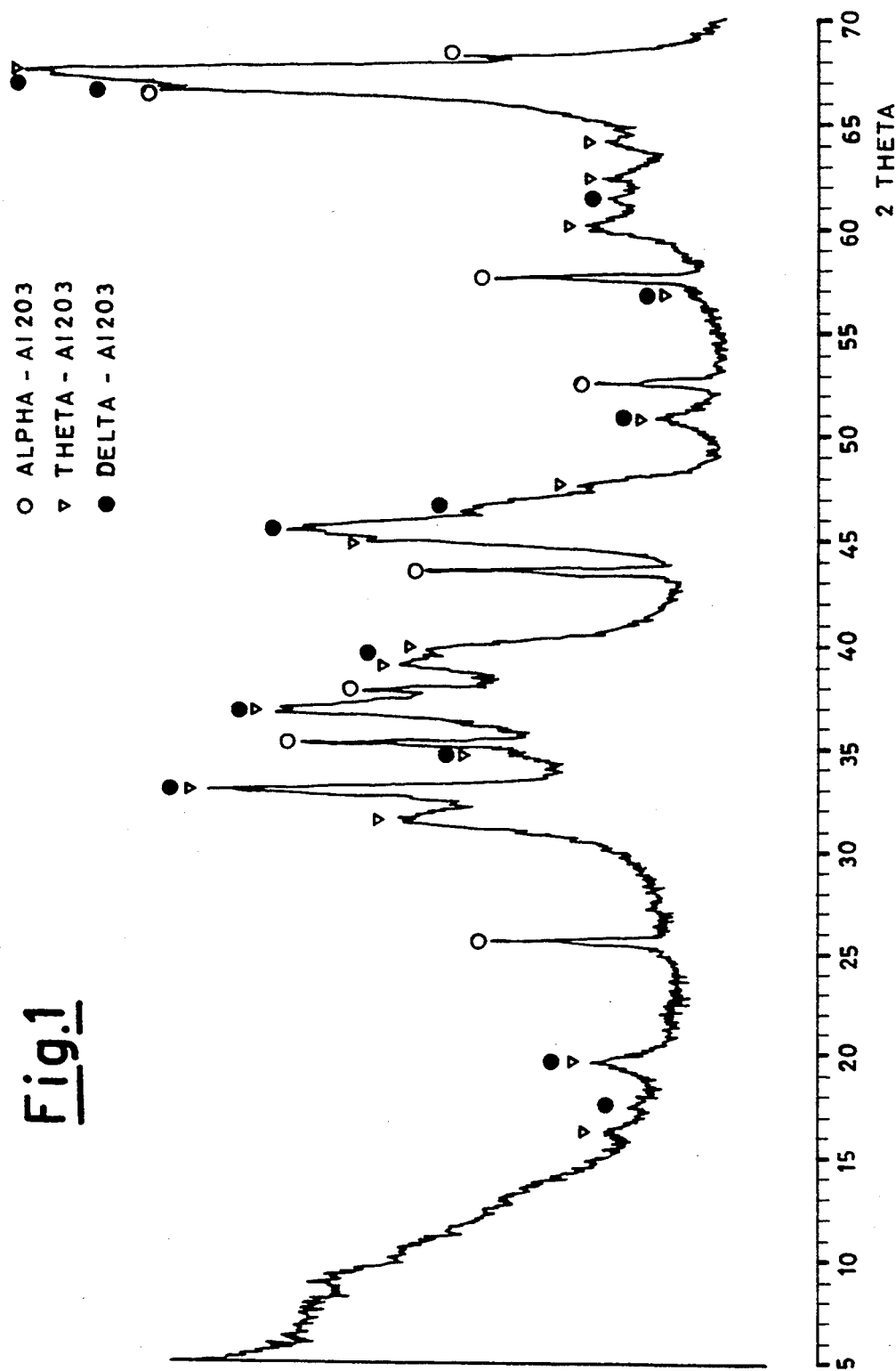
FIG. 1 is an x-ray diffraction spectrum of the microspheroidal pseudoboehmite containing added silica of Example 1.

During our experiments we have found that by applying said activation process to a particular catalytic composition, in itself new, the results obtained with known catalysts subjected to the aforedescribed process are further improved (especially the selectivity towards olefins).

Further according to the present invention, the catalytic composition for dehydrogenating $C_2$-$C_5$ paraffins containing gallium, alumina, silica and possibly one or more alkaline or alkaline-earth metals is characterised in that the gallium, expressed as $Ga_2O_3$, is contained in a quantity of between 0.10 and 33.6 wt % and preferably between 0.50 and 2.5%, the silica is contained in a quantity of between 0.08 and 3 wt %, and the alkaline metal, expressed as oxide, is contained in a quantity of between 0 and 5 wt %, the remainder to 100 being alumina in $\delta$ or $\theta$ phase or in $\delta+\theta$ or $\delta+\theta+\alpha$ phase mixture.

If an alkaline metal is used, potassium is preferred in a quantity preferably of between 0.1 and 1 wt % expressed as $K_2O$.

Said composition must be activated by the aforedescribed process. The process for preparing said composition consists essentially of dispersing a gallium compound over a support consisting of aluminum (in $\delta$ or $\theta$ phase or in $\delta+\theta$ or $\delta+\theta+\alpha$ phase mixture) and silica.

Some methods of dispersing the gallium over the support are given hereinafter, the invention however not being limited to these. The dispersion procedure can consist of impregnating said support with a solution containing gallium precursors followed by drying and calcining, or by ion exchange with a solution containing a gallium salt followed by liquid separation, drying and activation of the solid, or by surface adsorption of volatile gallium species with possible calcining of the solid.

Of the aforelisted, the preferred procedure is impregnation by the incipient wetness method or immersion of the support in the solution containing the precursor.

If an alkaline or alkaline-earth metal is used, the methods for its incorporation include the following:
  coimpregnation of the support
  adding the alkaline metal to the support before dispersing the gallium precursor
  treatment of the gallium-containing solid, ion exchange, impregnation etc. with the alkaline or alkaline-earth metal.

The present invention further relates to the use of a catalyst precursor activated by the aforedescribed process and containing gallium, alumina, possibly silica and/or one or more alkaline compounds, or the use of the aforedescribed catalytic composition activated by said process for the dehydrogenation of $C_2$-$C_5$ paraffins.

The paraffin dehydrogenation process is known in the art. $C_2$-$C_5$ paraffins are fed into a preferably fluidized bed reactor using a suitable catalyst and operating preferably at a temperature of between 450° and 700° C., at a pressure of between 1 and 2 kg/cm$^2$ with a GHSV of between 100 and 10000 h$^{-1}$ (hydrocarbon volume/hour ×liters of catalyst).

Some examples are given hereinafter, but are in no way to be considered as limitative of the present invention.

EXAMPLE 1

A microspheroidal pseudoboehmite with added silica (1.2 wt %) and having a particle diameter of between 5 and 200 μm is prepared by spray-drying an aluminium hydroxide suspension obtained by precipitation from a solution of an aluminium and silicon salt. A sample of the pseudoboehmite is subjected to controlled thermal treatment comprising initial calcining at 450° C. for one hour followed by further calcining at 1070° C. for 8 hours in a stream of steam-saturated air. The product obtained from the calcining has a specific surface of 100 m$^2$/g, a total porosity of 0.45 cc/g and consists of delta, theta and alpha transition aluminas as demonstrated by the XRD spectrum (FIG. 1). 150 g of this alumina were impregnated, using the incipient wetness procedure, with an aqueous solution obtained by dissolving 8.21 g of Ga(NO$_3$)3.9H$_2$O and 0.78 g of KNO$_3$ in 67.5 cc of deionized water. The impregnated substance was left for 24 hours at ambient temperature and then dried at 150° C. for 24 hours. The dried substance was then activated in a dry air stream at 600° C. for 4 hours.

The weight composition of the catalyst, in which both the gallium and the potassium are expressed as oxides, is 1.21% Ga$_2$O$_3$, 0.24% K$_2$O, 1.57% SiO$_2$, Al$_2$O$_3$ balance to 100. The catalyst performance in the fluidized bed dehydrogenation of propane and butane is shown in Tables 1 and 2 respectively. After the catalytic tests the same catalyst was further activated by subjecting it to the following cycle: oxidation with air for 60 minutes, purging with nitrogen for 3 minutes, reduction with hydrogen for 60 minutes at a temperature of 650° C. After 180 hours of activation by the stated procedure, it was again used for dehydrogenating the same paraffins (Tables 3 and 4).

Activation by oxidation and reduction cycles is applied to all the catalysts described in the following examples.

Table 5 shows the catalytic activity of said catalyst (and of those of the following examples) activated by the aforedescribed claimed procedure, in the dehydrogenation of isobutane operating under the same temperature and space velocity conditions as Example 2 of U.S. Pat. No. 4056576.

EXAMPLE 2

Figure 2:
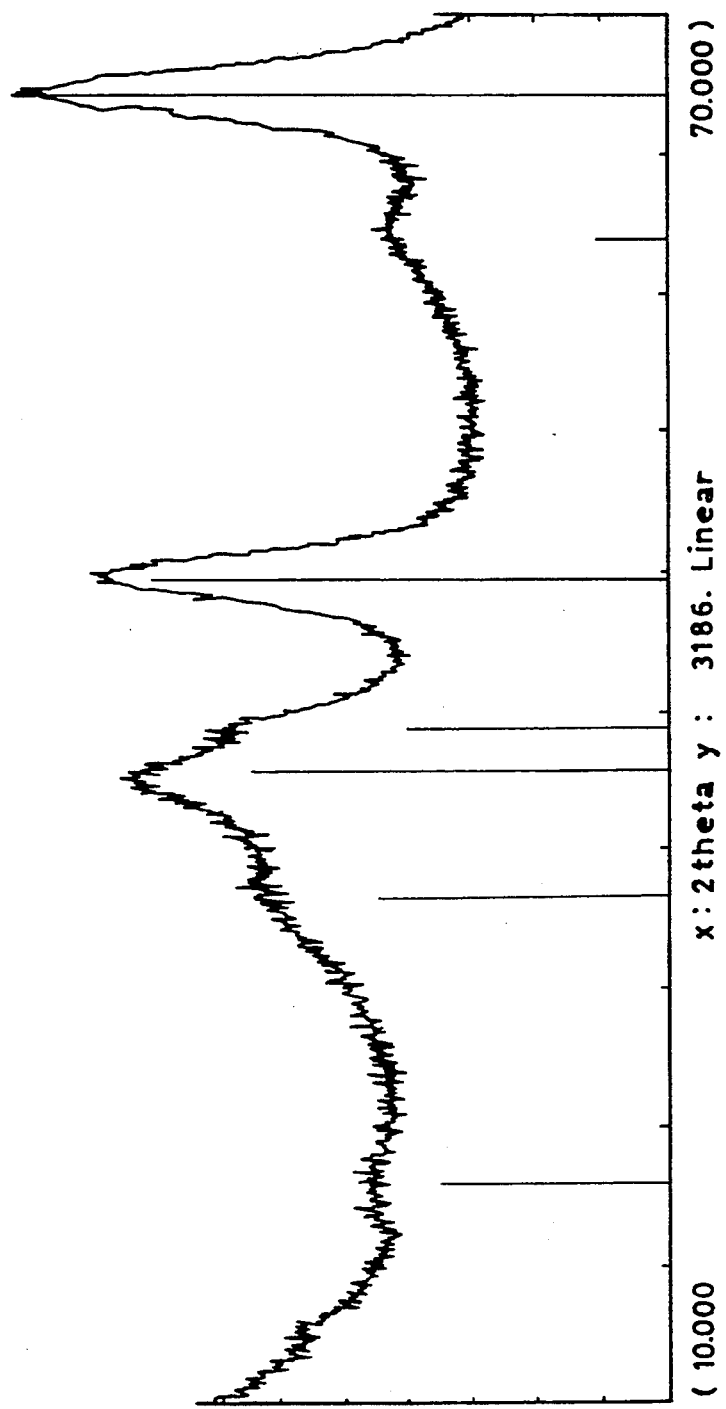
FIG. 2 is an x-ray diffraction spectrum of the gamma alumina of Example 2.

A gamma alumina (XRD spectrum FIG. 2) with a specific surface of 250 m$^2$/g and a total porosity of 0.55 cc/g is prepared by calcining a sample of the pseudoboehmite used in the preceding example at 450° C. for one hour and then at 650° C. for four hours in a stream of steam-saturated air. 150 g of gamma alumina were impregnated with 82.5 cc of an aqueous solution containing the same dissolved quantities of Ga(NO$_3$)3.9H$_2$O and KNO$_3$ as in Example 1, to obtain a catalyst prepared by the same procedure and having the same weight composition as the preceding example. The performance is given in Tables 1, 2, 3, 4 and 5.

EXAMPLE 3

150 g of calcined alumina comprising the components (delta, theta and alpha) of Example 1 are impregnated with an aqueous solution obtained by dissolving 8.18 g of Ga(NO$_3$)3.9H$_2$O in 67.5 cc of deionized water. The impregnation and the subsequent drying and activation were conducted by the known procedure (Example 1). The weight composition of the catalyst is 1.21% Ga$_2$O$_3$, 1.58% SiO$_2$, Al$_2$O$_3$ balance to 100.

The performance is summarized in Tables 1, 2, 3, 4 and 5.

EXAMPLE 4

Using the stated procedure a catalyst is prepared with a weight composition of 0.76% Ga$_2$O$_3$, 1.58% SiO$_2$, Al$_2$O$_3$ balance to 100, by impregnating 150 g of the alumina of Example 3 with an aqueous solution containing 4.5 g of dissolved Ga(NO$_3$)3.9H$_2$O. The catalytic performance of the system is summarized in Tables 1, 2, 3, 4 and 5.

EXAMPLE 5

The same quantity of the same alumina as used in Example 3 was impregnated with 67.5 cc of a solution containing 26.1 g of dissolved Ga(NO$_3$)3.9H$_2$O. The weight composition of the catalyst, prepared by the described procedure, is 3.76% Ga$_2$O$_3$, 1.54% SiO$_2$, Al$_2$O$_3$ balance to 100. The performance is shown in Tables 1, 2, 3, 4 and 5.

EXAMPLE 6

A sample of the same alumina as used in Example 2 was impregnated with an aqueous solution containing a suitable quantity of dissolved Ga(NO$_3$)3.9H$_2$O to obtain a catalyst with the following weight composition: 1.21% Ga$_2$O$_3$, 1.58% SiO$_2$, Al$_2$O$_3$ balance to 100. The performance obtained is shown in Tables 1, 2, 3, 4 and 5.

EXAMPLE 7

Figure 3:
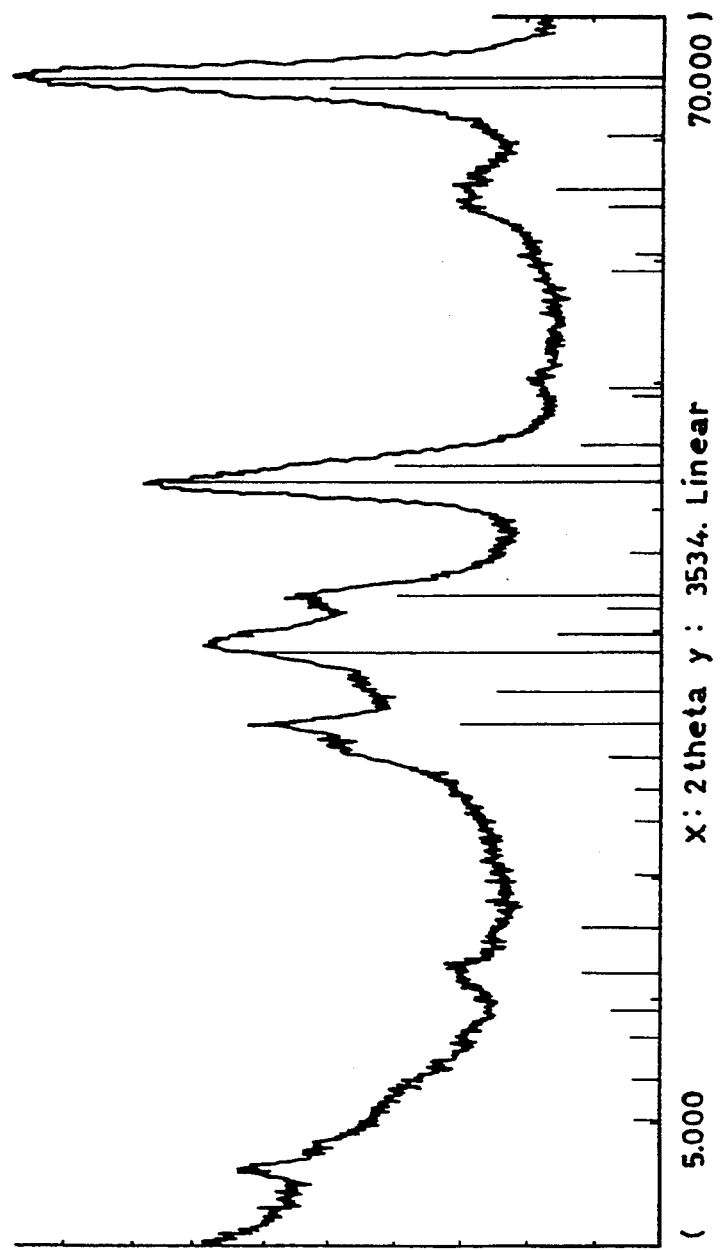
FIG. 3 is an x-ray diffraction spectrum of the pseudoboehmite which has a structural component of delta alumina of Example 7.

A sample of pseudoboehmite, produced as described in Example 1, is subjected to controlled thermal treatment comprising initial calcining at 450° C. for one hour followed by further calcining at 980° C. for 8 hours in a stream of steam-saturated air. The resultant product is characterised by a specific surface of 128 m²/g, a total porosity of 0.48 cc/g and consists structurally of delta alumina (XRD spectrum FIG. 3). 150 g of the calcined alumina were impregnated with 72 cc of an aqueous solution containing 8.18 g of dissolved $Ga(NO_3)_3 \cdot 9H_2O$. The weight composition of the catalyst, prepared by the procedure of Example 1, is 1.21% $Ga_2O_3$, 1.58% $SiO_2$, $Al_2O_3$ balance to 100. Its catalytic performance is summarized in Tables 1, 2, 3, 4 and 5.

EXAMPLE 8

Figure 4:
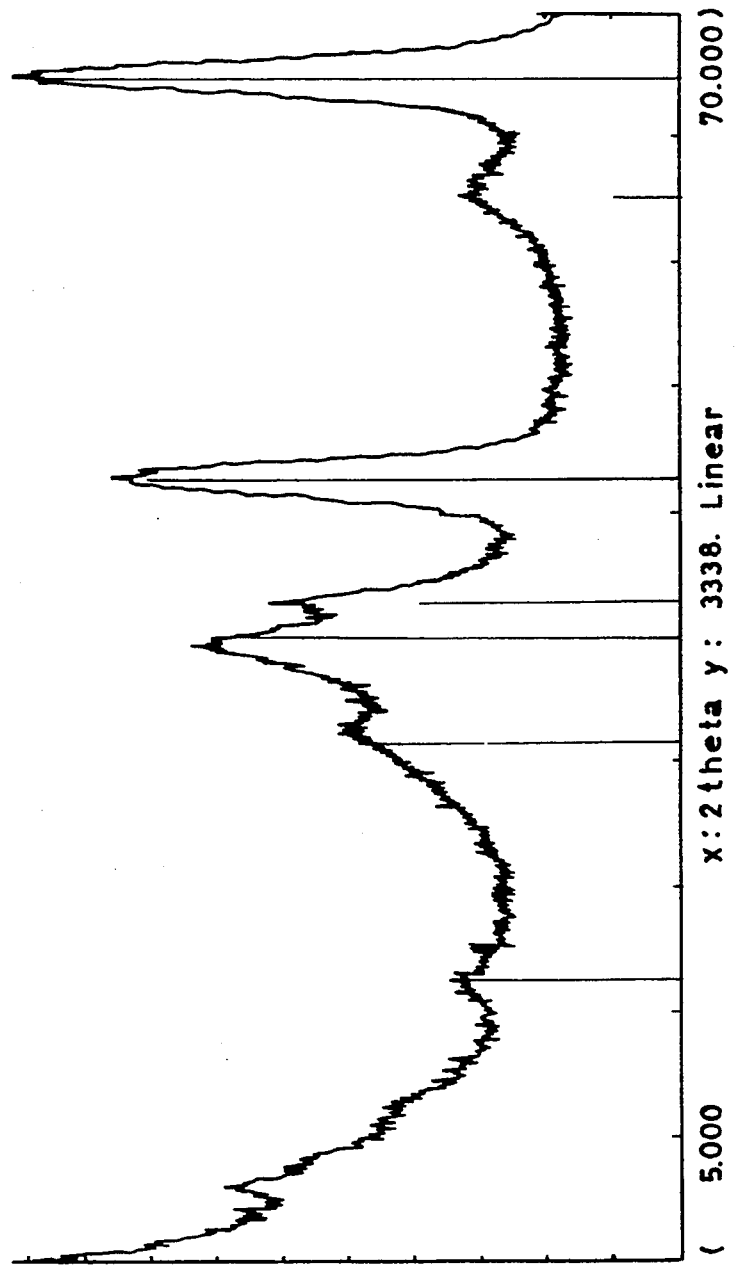
FIG. 4 is an x-ray diffraction spectrum of the microspheroidal pseudoboehmite of Example 8 which is silica free.

A sample of microspheroidal pseudoboehmite, prepared by the procedure described in Example 1 but silica-free, and with a particle diameter of 5–200 μm was calcined under the conditions described in Example 2. The calcined product is a gamma alumina, as shown by its diffraction spectrum of FIG. 4, with a specific surface of 200 m²/g and a total porosity of 0.52 cc/g. 150 g of the calcined alumina were impregnated with 78 cc of an aqueous solution containing 8.18 g of dissolved $Ga(NO_3)_3 \cdot 9H_2O$, using the same procedure for the impregnation, drying and calcining as already described in Example 1. The weight composition of the final catalyst is 1.21% $Ga_2O_3$, $Al_2O_3$ balance to 100. Its catalytic performance is summarized in Tables 1, 2, 3, 4 and 5.

EXAMPLE 9

150 g of microspheroidal silica with a particle diameter of 5–250 μm, a specific surface of 254 m²/g and a total porosity of 0.6 cc/g were impregnated with 90 cc of a solution containing the same quantity of $Ga(NO_3)_3 \cdot 9H_2O$ (Example 8). The catalyst was prepared using the preparation procedure of Example 1. The final composition of the catalyst was 1.21% $Ga_2O_3$, $SiO_2$ balance. The performance is give in Tables 1, 2, 3, 4 and 5.

TABLE 1

Catalytic activity after activation at 600° C. for 4 hours in air
Propane dehydrogenation
T = 590° C. GHSV = 400 h⁻¹

| | Examples | | | | | | | | |
|---|---|---|---|---|---|---|---|---|---|
| | 1 | 2 | 3 | 4 | 5 | 6 | 7 | 8 | 9 |
| wt % $SiO_2$ | 1.57 | 1.57 | 1.58 | 1.59 | 1.54 | 1.58 | 1.58 | abs. | 98.79 |
| wt % $K_2O$ | 0.24 | 0.24 | abs. | abs. | abs. | abs. | abs. | abs. | abs. |
| wt % $Ga_2O_3$ | 1.21 | 1.21 | 1.21 | 0.67 | 3.76 | 1.21 | 1.21 | 1.21 | 1.21 |
| wt % $Al_2O_3$ | bil. | bil. | bil. | bil. | bil. | bil. | bil. | bil. | abs. |
| % $C_3H_8$ CONV | 10 | 6 | 12 | 9.5 | 26 | 9 | 12 | 19 | 14 |
| wt % $C_3H_6$ Sel. | 76 | 50 | 77 | 82 | 60 | 58 | 68 | 56 | 74 |
| wt % $C_3H_6$ yield | 7.6 | 3 | 9.3 | 7.8 | 15.6 | 5.2 | 8.2 | 10.6 | 10.4 |
| wt % Sel. (BTX) | abs. | abs. | abs. | abs. | 5 | abs. | abs. | 2 | abs. |

TABLE 2

Catalytic activity after activation at 600° C. for 4 hours in air
Isobutane dehydrogenation
T = 580° C. GHSV = 400 h⁻¹

| | Examples | | | | | | | | |
|---|---|---|---|---|---|---|---|---|---|
| | 1 | 2 | 3 | 4 | 5 | 6 | 7 | 8 | 9 |
| wt % $SiO_2$ | 1.57 | 1.57 | 1.58 | 1.59 | 1.54 | 1.58 | 1.58 | abs. | 98.79 |
| wt % $K_2O$ | 0.24 | 0.24 | abs. | abs. | abs. | abs. | abs. | abs. | abs. |
| wt % $Ga_2O_3$ | 1.21 | 1.21 | 1.21 | 0.67 | 3.76 | 1.21 | 1.21 | 1.21 | 1.21 |
| wt % $Al_2O_3$ | bil. | bil. | bil. | bil. | bil. | bil. | bil. | bil. | abs. |
| % i-$C_4$ CONV | 34 | 32 | 40 | 35 | 40 | 38 | 28 | 44 | 10 |
| wt % i-$C_4$ Sel. | 83 | 50 | 63 | 74 | 40 | 41 | 55 | 25 | 58 |
| wt % i-$C_4$ Sel.* | 86 | 58 | 72 | 84 | 55 | 58 | 69 | 44 | 80 |
| wt % i-$C_4$ yield | 28.2 | 16 | 25.2 | 25.9 | 16 | 15.6 | 15.4 | 11 | 5.8 |
| wt % i-$C_4$ yield* | 29.2 | 18.6 | 28.8 | 29.4 | 22 | 22.1 | 19.3 | 19.4 | 8 |
| wt % Sel. (BTX) | abs. | 5 | 8.9 | 1 | 13 | 1.8 | 6.4 | 11 | 4 |

*i $C_4H_8$ + $C_4H_8$ + 2 CiS $C_4H_8$ + trans $C_4H_8$

TABLE 3

Catalytic activity after 180 hours of activation in oxidation/reduction cycles
Propane dehydrogenation
T = 590° C. GHSV = 400 h⁻¹

| | Examples | | | | | | | | |
|---|---|---|---|---|---|---|---|---|---|
| | 1 | 2 | 3 | 4 | 5 | 6 | 7 | 8 | 9 |
| wt % $SiO_2$ | 1.57 | 1.57 | 1.58 | 1.59 | 1.54 | 1.58 | 1.58 | abs. | 98.79 |
| wt % $K_2O$ | 0.24 | 0.24 | abs. | abs. | abs. | abs. | abs. | abs. | abs. |
| wt % $Ga_2O_3$ | 1.21 | 1.21 | 1.21 | 0.67 | 3.76 | 1.21 | 1.21 | 1.21 | 1.21 |
| wt % $Al_2O_3$ | bil. | bil. | bil. | bil. | bil. | bil. | bil. | bil. | abs. |
| % $C_3H_8$ CONV | 33 | 30 | 39 | 30 | 24 | 37 | 31 | 29 | 10 |
| wt % $C_3H_6$ Sel. | 89 | 82 | 84 | 85 | 76 | 77 | 81 | 60 | 67 |
| wt % $C_3H_6$ yield | 29.4 | 24.6 | 32.7 | 25.5 | 18.2 | 28.5 | 25.1 | 17.4 | 6.7 |
| wt % Sel. (BTX) | 0.5 | 0.2 | 2.5 | 0.1 | 1 | 1.8 | 1.1 | 3.6 | 3.5 |

TABLE 4

Catalytic activity after 180 hours of activation in oxidation and reduction cycles
Isobutane dehydrogenation
T = 580° C. GHSV = 400 h$^{-1}$

| | Examples | | | | | | | | |
|---|---|---|---|---|---|---|---|---|---|
| | 1 | 2 | 3 | 4 | 5 | 6 | 7 | 8 | 9 |
| wt % SiO$_2$ | 1.57 | 1.57 | 1.58 | 1.59 | 1.54 | 1.58 | 1.58 | abs. | 98.79 |
| wt % K$_2$O | 0.24 | 0.24 | abs. | abs. | abs. | abs. | abs. | abs. | abs. |
| wt % Ga$_2$O$_3$ | 1.21 | 1.21 | 1.21 | 0.67 | 3.76 | 1.21 | 1.21 | 1.21 | 1.21 |
| wt % Al$_2$O$_3$ | bil. | bil. | bil. | bil. | bil. | bil. | bil. | bil. | abs. |
| % i-C$_4$ CONV | 48 | 46 | 52 | 41 | 38 | 53 | 43 | 44 | 16 |
| wt % i-C$_4$ Sel. | 87 | 67 | 67 | 69 | 50 | 54.5 | 65 | 31 | 55 |
| wt % i-C$_4$ Sel.* | 90 | 77 | 80 | 82 | 65 | 68.4 | 78 | 48 | 77 |
| wt % i-C$_4$ yield | 41.7 | 30.8 | 34.8 | 28.3 | 19 | 28.8 | 27.9 | 13.6 | 8.8 |
| wt % i-C$_4$ yield* | 43.2 | 35.4 | 41.6 | 33.6 | 24.7 | 36.3 | 33.5 | 21 | 12.3 |
| wt % Sel. (BTX) | 1 | 4.6 | 3.4 | 2.6 | 8 | 8.5 | 4.7 | 13.5 | 3.2 |

*i C$_4$H$_8$ + C$_4$H$_8$ + 2 CiS C$_4$H$_8$ + trans C$_4$H$_8$

TABLE 5

Catalytic activity after 180 hours of activation in oxidation and reduction cycles
Isobutane dehydrogenation
T = 550° C. GHSV = 570 h$^{-1}$

| | Examples | | | | | | | | |
|---|---|---|---|---|---|---|---|---|---|
| | 1 | 2 | 3 | 4 | 5 | 6 | 7 | 8 | 9 |
| wt % SiO$_2$ | 1.57 | 1.57 | 1.58 | 1.59 | 1.54 | 1.58 | 1.58 | abs. | 98.79 |
| wt % K$_2$O | 0.24 | 0.24 | abs. | abs. | abs. | abs. | abs. | abs. | abs. |
| wt % Ga$_2$O$_3$ | 1.21 | 1.21 | 1.21 | 0.67 | 3.76 | 1.21 | 1.21 | 1.21 | 1.21 |
| wt % Al$_2$O$_3$ | bil. | bil. | bil. | bil. | bil. | bil. | bil. | bil. | abs. |
| % i-C$_4$ CONV | 40 | 38 | .43 | 36 | 25 | 45 | 34 | 36 | 8.4 |
| wt % i-C$_4$ Sel. | 93 | 82 | 78 | 80 | 65 | 68 | 78 | 36 | 72 |
| wt % i-C$_4$ Sel.* | 94 | 87.8 | 85 | 86 | 79 | 79 | 87 | 52 | 88 |
| wt % i-C$_4$ yield | 37.2 | 31.2 | 33.5 | 28.8 | 16.3 | 30.6 | 26.5 | 13 | 6 |
| wt % i-C$_4$ yield* | 37.6 | 33.4 | 36.5 | 31 | 19.8 | 35.5 | 29.6 | 18.7 | 7.4 |
| wt % Sel. (BTX) | 0.2 | 1.2 | 2.3 | 1.3 | 4 | 4.2 | 1.6 | 12 | 1.2 |

*i C$_4$H$_8$ + C$_4$H$_8$ + 2 CiS C$_4$H$_8$ + trans C$_4$H$_8$

We claim:

1. In a process for the catalytic dehydrogenation of light paraffins, the improvement comprising:
catalytically dehydrogenating light hydrocarbons over a catalyst composition comprising gallium, alumina, silica and optionally at least one alkali or alkaline-earth metal, wherein gallium expressed as Ga$_2$O$_3$, is present in an amount of from 0.1 to 33.6 wt. %, the silica is present in an amount of from 0.08 to 3 wt. % and the alkali metal, expressed as the oxide, is present in an amount of from 0 to 5 wt. %, the remainder up to 100 being alumina in the δ or θ phase or in the δ+θ or δ+θ+α phase mixture, said catalytic composition being activated by an activating process comprising thermally activating the catalyst in the air at a temperature of between 450° and 1,000° C., said activation treatment being followed by a post activation treatment effected as follows:
oxidizing the activated catalyst with air, oxygen, or mixtures thereof, or a mixture containing oxygen at least in a 5 volume % concentration in an inert gas, for a time of between 1 and 180 minutes, at a temperature of between 500° and 1,000° C. in a vessel;
purging the vessel and catalyst therein with an inert gas for a time of between 1 and 10 minutes; and
reducing the catalyst with hydrogen or a mixture containing hydrogen in at least a 10 volume % concentration in an inert or reducing gas, for a time of between 1 and 120 minutes, at a temperature of between 450° and 800° C.

2. The process of claim 1 wherein gallium, expressed as Ga$_2$O$_3$, is between 0.5 and 2.5 weight % based on the total catalyst weight.

3. The process of claim 1 wherein said alkali metal is potassium.

4. The process of claim 3 wherein said potassium, expressed as K$_2$O is between 0.1 and 1 weight % based on the total catalyst weight.

5. The process of claim 1 comprising effecting the oxidizing for a period of time of between 30 and 90 minutes at a temperature of between 500° C. and 700° C., effecting the purging for a time of between 3 and 5 minutes, and effecting the reducing for a time of between 30 and 90 minutes at a temperature of between 500° C. and 700° C.

6. The process of claim 2 comprising effecting the oxidizing for a period of time of between 30 and 90 minutes at a temperature of between 500° C. and 700° C., effecting the purging for a time of between 3 and 5 minutes, and effecting the reducing for a time of between 30 and 90 minutes at a temperature of between 500° C. and 700° C.

7. The process of claim 3 comprising effecting the oxidizing for a period of time of between 30 and 90 minutes at a temperature of between 500° C. and 700° C., effecting the purging for a time of between 3 and 5 minutes, and effecting the reducing for a time of between 30 and 90 minutes at a temperature of between 500° C. and 700° C.

8. The process of claim 4 comprising effecting the oxidizing for a period of time of between 30 and 90 minutes at a temperature of between 500° C. and 700° C., effecting the purging for a time of between 3 and 5 minutes, and effecting the reducing for a time of between 30 and 90 minutes at a temperature of between 500° C. and 700° C.

9. The process of claim 1 wherein said light paraffin is a $C_2$–$C_5$ paraffin

10. The process of claim 2 wherein said light paraffin is a $C_2$–$C_5$ paraffin.

11. The process of claim 3 wherein said light paraffin is a $C_2$–$C_5$ paraffin.

12. The process of claim 4 wherein said light paraffin is a $C_2$–$C_5$ paraffin.

13. The process of claim 5 wherein said light paraffin is a $C_2$–$C_5$ paraffin.

14. In a process for the catalytic dehydrogenation of a light paraffin to an alkene the improvement comprising:
    catalytically dehydrogenating said light paraffin over a catalyst composition comprising gallium, alumina and optionally an alkali metal, wherein gallium, expressed as $Ga_2O_3$, is present in an amount of between 0.1 and 33.6 wt. %, the alkali metal is present in an amount of up to 5 wt. %, the remainder of the catalyst composition up to 100 being alumina, said catalyst having been activated by heating in air at a temperature of from about 450° C. to 1000° C., followed successively by oxidizing the catalyst in an oxygen-containing gas and reducing the oxidized catalyst by exposure of the catalyst to the reducing gas mixture comprising hydrogen, wherein the conversion rate of said paraffin is about 24 wt. % or more, and wherein the selectivity of the catalyst with respect to the alkene is greater than 40 wt. %.

15. The process of claim 14 wherein gallium is present in an amount of from 0.5 to about 2.5 weight percent.

16. The process of claim 14 wherein said light paraffin is isobutane, said alkene is isobutene, said conversion is greater than 40 weight %, and said selectivity is greater than 40 weight % to isobutene.

* * * * *